United States Patent
Weaner et al.

(10) Patent No.: US 8,357,080 B2
(45) Date of Patent: Jan. 22, 2013

(54) TISSUE CONTRASTING GASTRIC BAND

(75) Inventors: Lauren S. Weaner, Beavercreek, OH (US); Christopher W. Widenhouse, Clarksville, OH (US); Jeffrey P. Wiley, Milford, OH (US); Kevin R. Doll, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1042 days.

(21) Appl. No.: 11/798,498

(22) Filed: May 14, 2007

(65) Prior Publication Data

US 2008/0287975 A1    Nov. 20, 2008

(51) Int. Cl.
*A61F 2/00* (2006.01)

(52) U.S. Cl. .......... 600/37; 600/31; 604/909; 606/157

(58) Field of Classification Search ............ 600/29–32, 600/37; 604/909; 606/157
See application file for complete search history.

(56) References Cited

U.S. PATENT DOCUMENTS

| 4,634,443 | A | * | 1/1987 | Haber | 600/31 |
| 5,006,106 | A | * | 4/1991 | Angelchik | 600/37 |
| 2005/0043751 | A1 | * | 2/2005 | Phan et al. | 606/155 |
| 2007/0250020 | A1 | * | 10/2007 | Kim et al. | 604/264 |

FOREIGN PATENT DOCUMENTS

| FR | 2887436 | 12/2006 |
| WO | WO98/56321 | 12/1998 |
| WO | WO2004/041133 | 5/2004 |
| WO | WO2006/014496 | 2/2006 |

* cited by examiner

*Primary Examiner* — Charles A Marmor, II
*Assistant Examiner* — Carrie R Dorna

(57) ABSTRACT

A balloon-type gastric band that includes a balloon and a belt secured to the balloon. The balloon includes a mechanism for contrasting the balloon from surrounding tissue when placed within a patient.

10 Claims, 4 Drawing Sheets

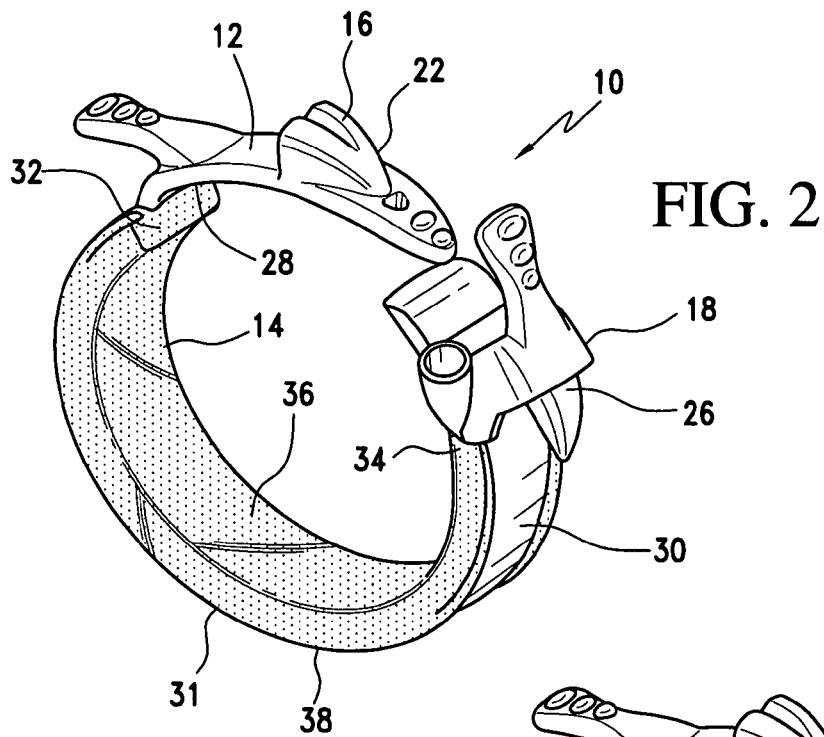
FIG. 2
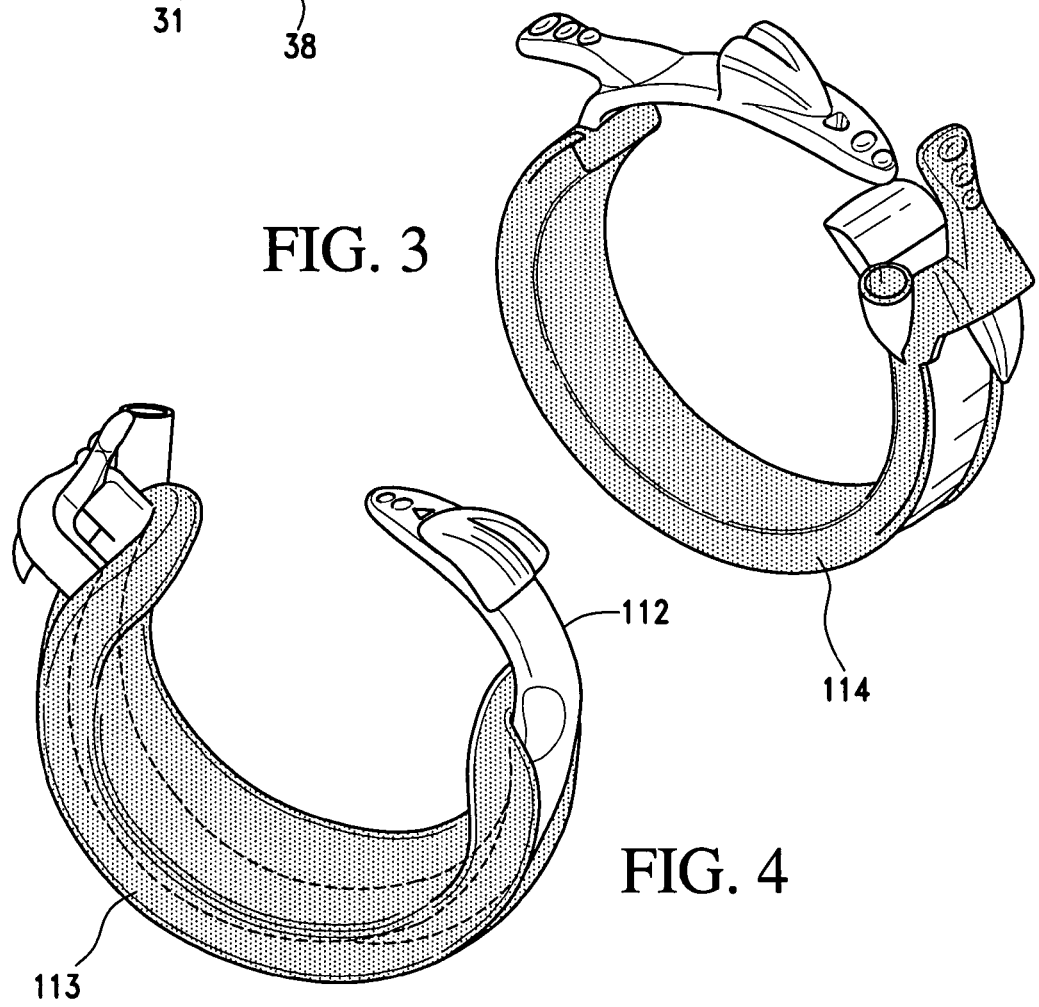
FIG. 3
FIG. 4

TISSUE CONTRASTING GASTRIC BAND

BACKGROUND OF THE INVENTION

1. Field of the Invention

The invention relates to a gastric band having a mechanism for providing a contrast in color with adjacent tissue.

2. Description of the Related Art

Morbid obesity is a serious medical condition. In fact, morbid obesity has become highly pervasive in the United States, as well as other countries, and the trend appears to be heading in a negative direction. Complications associated with morbid obesity include hypertension, diabetes, coronary artery disease, stroke, congestive heart failure, multiple orthopedic problems and pulmonary insufficiency with markedly decreased life expectancy. With this in mind, and as those skilled in the art will certainly appreciate, the monetary and physical costs associated with morbid obesity are substantial. In fact, it is estimated the costs relating to obesity are in excess of one hundred billion dollars in the United States alone.

A variety of surgical procedures have been developed to treat obesity. The most common currently performed procedure is Roux-en-Y gastric bypass (RYGB). This procedure is highly complex and is commonly utilized to treat people exhibiting morbid obesity. Other forms of bariatric surgery include Fobi pouch, bilio-pancreatic diversion, and gastroplastic or "stomach stapling". In addition, implantable devices are known which limit the passage of food through the stomach and affect satiety.

In view of the highly invasive nature of many of these procedures, efforts have been made to develop less traumatic and less invasive procedures. Gastric-banding is one of these methods. Gastric-banding is a type of gastric reduction surgery attempting to limit food intake by reducing the size of the stomach. In contrast to RYGB and other stomach reduction procedures, gastric-banding does not require the alteration of the anatomy of the digestive tract in the duodenum or jejunum.

Since the early 1980's, gastric bands have provided an effective alternative to gastric bypass and other irreversible surgical weight loss treatments for the morbidly obese. Several alternate procedures are performed under the heading of gastric-banding. Some banding techniques employ a gastric ring, others use a band, some use stomach staples and still other procedures use a combination of rings, bands and staples. Among the procedures most commonly performed are vertical banded gastroplasty (VBG), silastic ring gastroplasty (SRG) and adjustable silastic gastric banding (AGB).

In general, the gastric band is wrapped around an upper portion of the patient's stomach, forming a stoma that is less than the normal interior diameter of the stomach. This restricts food passing from an upper portion to a lower digestive portion of the stomach. When the stoma is of an appropriate size, food held in the upper portion of the stomach provides a feeling of fullness that discourages overeating.

More particularly, and in practice, the gastric band is inserted behind the stomach and the ends of the gastric band are coupled to latch the device about the stomach. It is, however, often difficult to visualize the gastric band as this is being done. As such, a need exists for mechanisms to improve one's ability to visualize a gastric band as it is being secured about a patient's stomach. The present invention provides such a mechanism.

SUMMARY OF THE INVENTION

It is, therefore, an object of the present invention to provide a balloon-type gastric band that includes a balloon and a belt secured to the balloon. The balloon includes at least one colored section and at least one clear section for respectively contrasting the balloon from surrounding tissue when placed within a patient and facilitating identification of leaks within the balloon.

It is also an object of the present invention to provide a balloon-type gastric band wherein the at least one colored section includes a spiral.

It is another object of the present invention to provide a balloon-type gastric band wherein the at least one colored section is radiopaque.

It is a further object of the present invention to provide a balloon-type gastric band wherein the at least one colored section includes a stripe.

It is also another object of the present invention to provide a balloon-type gastric band wherein the at least one colored section includes a colored pad print.

It is still another object of the present invention to provide a balloon-type gastric band including a balloon and a belt secured to the balloon, wherein at least one of the balloon or the belt is clear and the other is colored.

It is also an object of the present invention to provide a balloon-type gastric band wherein the belt is clear and the balloon is colored.

It is also a further object of the present invention to provide a balloon-type gastric band wherein the balloon is clear and the belt is colored.

It is yet a further object of the present invention to provide a balloon-type gastric band including a balloon and a belt secured to the balloon, wherein the balloon is colored while remaining translucent.

It is also an object of the present invention to provide a balloon-type gastric band wherein the supply tube includes a contrast agent incorporated therein.

It is another object of the present invention to provide a balloon-type gastric band wherein the contrast agent is radiopaque.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 2 is a perspective view of the gastric band shown in FIG. 1.

FIG. 3 is a perspective view of an alternate embodiment of a gastric band in accordance with the present invention.

FIG. 4 is a perspective view of yet another embodiment of a gastric band in accordance with the present invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Figure 1:
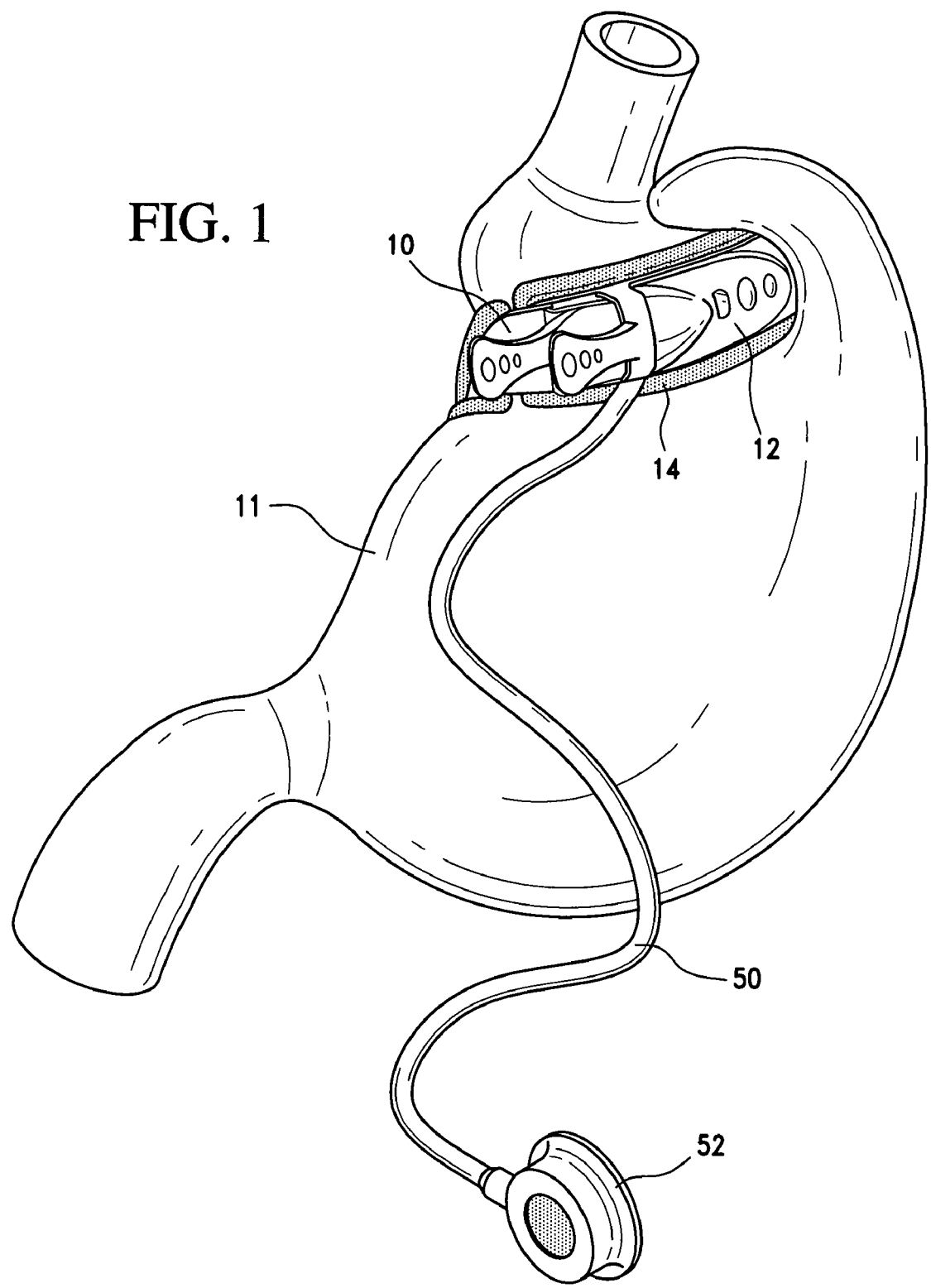
FIG. 1 is a perspective view of a gastric band in accordance with the present invention secured about a stomach.

Referring to FIGS. 1 and 2, a balloon-type gastric band 10 is disclosed in accordance with a preferred embodiment of the present invention. The gastric band 10 is generally composed of a reinforcing belt 12 to which an elongated balloon 14 is secured. The belt 12 includes a first end 16 and a second end 18 to which first and second latching members 22, 26 are respectively secured. In accordance with a preferred embodiment the first and second latching members 22, 26 are shaped and dimensioned for selective engagement, and are the same as disclosed in commonly owned U.S. patent application Ser. No. 11/182,072, entitled "Latching Device for Gastric Band", filed Jul. 15, 2005, which is incorporated herein by reference.

In accordance with a preferred embodiment, the belt 12 and balloon 14 are constructed as disclosed in commonly owned U.S. patent application Ser. No. 11/364,361, filed Mar. 1, 2006, entitled "Gastric Band", which is incorporated herein by reference. Generally, the belt 12 further includes an inner surface 28 and an outer surface 30. The outer surface 30 is substantially smooth and forms a substantial portion of the outer surface 31 of the gastric band 10 when it is secured about a patient's stomach 11 as shown in FIG. 1. The inner surface 28 of the belt 12 is shaped and dimensioned for attachment to the outer surface 38 of the balloon 14.

With regard to the balloon 14, it also includes a first end 32, a second end 34, an inner surface 36 and an outer surface 38. The inner surface 36 is substantially smooth and is shaped and dimensioned for engaging the patient's stomach when the gastric band 10 is secured thereto. The outer surface 38 of the balloon 14 is shaped and dimensioned for coupling with the inner surface 28 of the belt 12.

Regardless of how the gastric band 10 is molded or assembled together, the belt 12 and balloon 14 components may consist of the same materials or different materials (material durometer, fillers such as $BaSO_4$, $TiO_2$, colorants, etc.). In addition, features within the component (for example, the first and second latching members of the latching assembly) may vary in composition. These features may be adhered to the rest of the product with adhesive, mechanical fastening (i.e., snap fits), welding, co-molding, or overmolding. Although the belt 12 is disclosed as being secured to an outer surface 38 of the balloon 14, it is contemplated the belt 12 may be internal or external to the balloon surface or integrated into the balloon, without departing from the spirit of the present invention.

The balloon 14 of the present gastric band 10 is designed such that it visually contrasts with adjacent tissue while the gastric band 10 is being secured about the stomach, but is also optically translucent. By providing a balloon 14 which is both contrasting with adjacent tissue and optically translucent, the medical practitioner is able to take advantage of both features. In particular, the contrast color of the balloon 14 improves visualization of the balloon 14, and ultimately the gastric band 10, during a procedure. In addition, the color agent may be radiopaque, permitting postoperative monitoring of the gastric band 10. The fact the balloon is optically translucent, allows the medical practitioner to readily check for leaks in a conventional manner.

In accordance with a preferred embodiment, and with reference to FIG. 2, the balloon 14 is a milky contrast color, but is translucent such that the interior of the balloon 14 can be viewed while also creating a contrasting color when set adjacent tissue. In accordance with the present disclosure, it should be understood the term "milky color" is used to describe a balloon 14 providing both color (that is, a distinguishing pigment) while retaining the translucent qualities of an entirely clear film. The degree of contrasting color in the balloon 14 is controlled by one of any number of different contrast agents, such as, $BaSO_4$, $TiO_2$ or Ta, incorporated into the material from which the balloon 14 is composed. With this in mind and with reference to an alternate embodiment shown in FIG. 3, the balloon 114 may be loaded with more contrast agent, resulting in a balloon 114 exhibiting a darker color when compared to the balloon 14 shown in FIG. 2. In addition, either balloon 14, 114 may include, or not include, radiopaque filler materials.

In addition to the color of the balloon providing a contrast with adjacent tissue as the gastric band is being secured about the stomach, the contrast color also functions to hide manufacturing artifacts, such as adhesive necessary for assembly, parting lines, witness lines and/or assembly features. For example, and with reference to an embodiment shown with reference to FIG. 4, the contrast of the balloon 113 helps to hide the belt 112, which is shown in phantom lines, providing a more aesthetically desirable construction.

Figure 5:
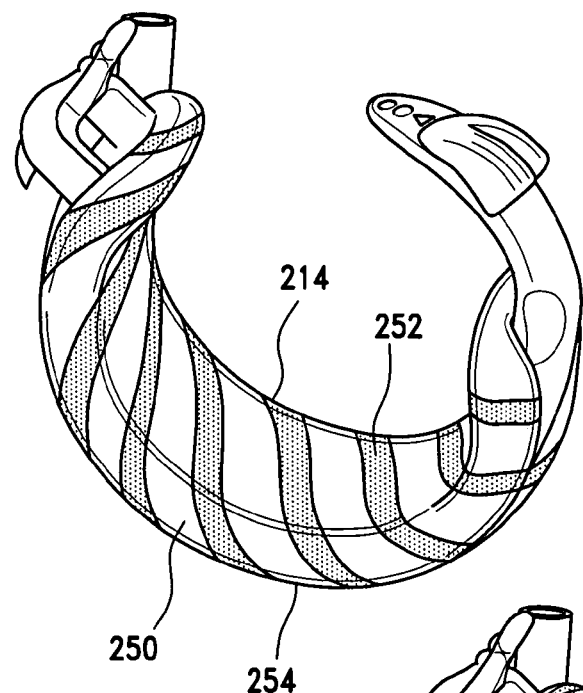
FIGS. 5, 6, 7 and 8 are additional embodiments of gastric bands including colored and clear sections in accordance with the present invention.
Figure 6:
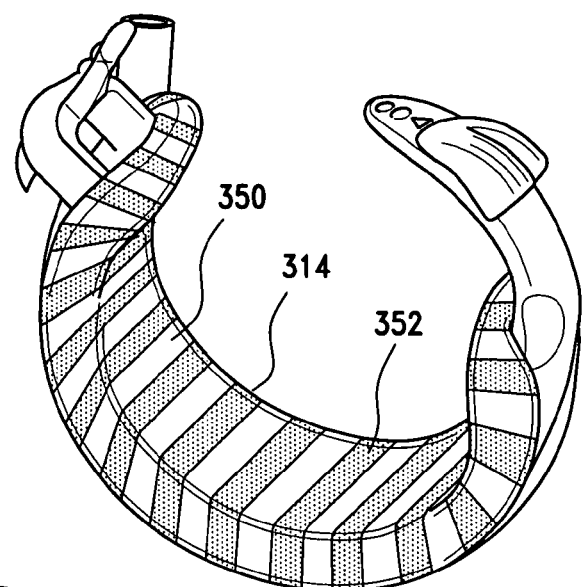
Figure 7:
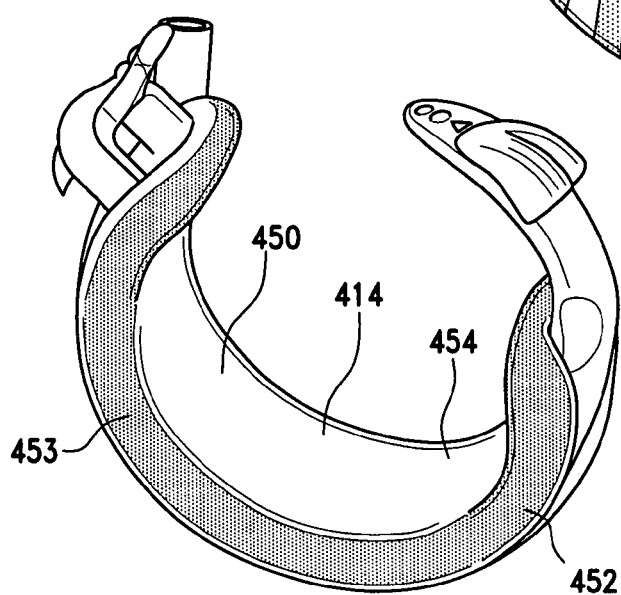

With reference to various other embodiments shown in FIGS. 5, 6 and 7, the balloons 214, 314, 414 are provided with a contrast mechanism by treating them to include both clear sections 250, 350, 450 and contrasting colored (for example, white and radiopaque) sections 252, 352, 452. The contrasting colored sections 252, 352, 452 could be spiraled (see FIG. 5), striped (see FIGS. 6 and 7) or otherwise uniquely formed upon the clear substrate, that is, the base material of the balloon, 254, 354, 454. For example, and with reference to FIG. 7, if stripes of the white, colored sections 452 were placed so that they were at the edges 453 of the balloon 414, that is, the laterally opposed sides of the balloon 414, when it was deflated, the surgeon would be able to see the balloon edges 453 against tissue when it was deflated, but the balloon 414 would still be primarily clear due to the remaining clear sections 450.

The clear sections 250, 350, 450 are relatively transparent portions of the balloon 214, 314, 414 that allow the medical practitioner to check for leaks or air bubbles in the balloon 214, 314, 414 during the procedure in a traditional manner. As those skilled in the art will appreciate, the clear sections 250, 350, 450 may vary in their transparency, but will ultimately be sufficiently transparent to allow a medical practitioner to monitor the internal structure of the balloon 214, 314, 414 for leaks in a traditional manner.

The radiopaque, white colored sections 252, 352, 452 are used postoperatively as a non-invasive diagnostic tool for evaluating either leaks in the balloon 214, 314, 414 or whether the balloon 214, 314, 414 remains structurally intact. The colored sections 252, 352, 452 also allow for improved visualization during the procedure. Although white, colored sections are disclosed herein in accordance with a preferred embodiment of the present invention, those skilled in the art will appreciate the colored sections may take on a variety of colors and hues without departing from the spirit of the invention. In general, however, the specific color chosen for use in accordance with various applications should be chosen to enhance visualization, whether that visualization be postoperative visualization by means of an external diagnostic tool or actual visualization of the balloon 214, 314, 414 during the surgical procedure.

It is contemplated the contrasting white, colored sections 252, 352, 452 and the clear sections 250, 350, 450 shown with reference to the embodiments of FIGS. 5, 6 and 7 would be combined in the balloon via co-extrusion, assembly, pad printing, overmolding, or (in the case of the milky balloon) combined in the base material and used in any traditional molding method.

Figure 8:
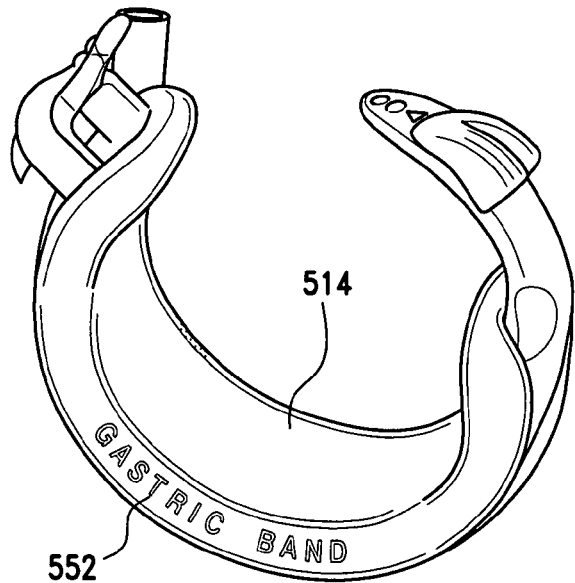

In addition to including a combination of clear sections and contrasting white, colored sections, the balloon 514 may also include a third color of pad print 552 (as shown in FIG. 8). The pad print 552 would consist of, for example, texts such as the product name or instructions for the surgeon. In addition to the contrasting agent used in creating the colored sections assisting in contrasting the balloon with adjacent tissue, the contrasting agent could also incorporate other functionalities such as, MRI visibility, lubricity, reliability properties, improved adhesive bonding and/or antimicrobial properties. As those skilled in the art will certainly appreciate the pad print may be combined with either the contrasting color as shown with reference to FIGS. 1, 2, 3 or 4, or the clear and colored sections shown with reference to FIGS. 5, 6 and 7.

Figure 10:
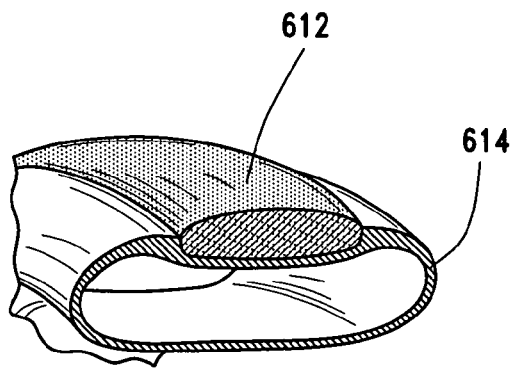
FIGS. 9 and 10 are respectively a perspective view and a cross sectional view of a gastric band in accordance with yet another embodiment of the present invention.
Figure 9:
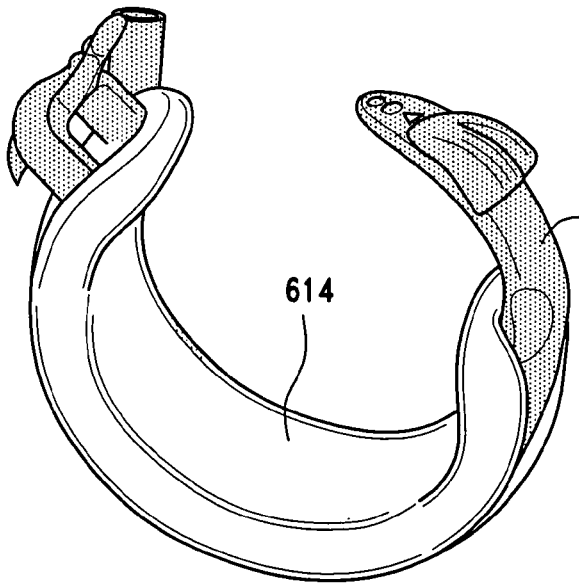
Figure 11:
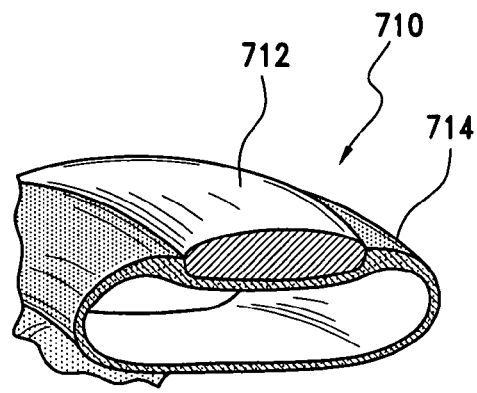
FIG. 11 is a cross sectional view of a gastric band in accordance with still a further embodiment of the present invention.

In accordance with an alternate embodiment, and with reference to FIGS. 9 and 10, the belt 612 may be constructed with a contrasting color and the balloon 614 made entirely clear. In this scenario, the belt 614 would include radiopaque agents for postoperative diagnostics (as well as visual feedback during gastric suturing) and the balloon 614 would be clear allowing one to see therein. Or, and with reference to FIG. 11, the belt 712 could be clear and the balloon 714 could be a solid contrasting color. In such a scenario, the balloon 714 would also include a radiopaque agent and could be used for postoperative diagnostics (as well as visual feedback during gastric suturing) and the belt 712 would be the optically translucent portion of the gastric band 710 to allow the surgeon to see inside the belt 712.

In each of the embodiments described above, the contrasting, colored section(s) of the gastric band may or may not be radiopaque. Where the colored section(s) is radiopaque, the gastric band will allow for a medical practitioner to visualize leaks in the balloon prior to or during the application procedure due to the clear sections or translucent nature of the material, while the radiopaque colored sections or radiopaque milky balloon permit postoperatively as a non-invasive diagnostics (for evaluating either leaks or erosion of the balloon).

In accordance with a preferred embodiment of the present invention, the belt and balloon are manufactured from biocompatible materials commonly used in the manufacture of gastric bands, for example, silicone, although those skilled in the art will appreciate a variety of polymers could be utilized in the manufacture of the gastric bands without departing from the spirit of the present invention.

Regardless of which embodiment is employed, the balloon is constructed to enhance contact with the stomach wall when applied thereto. With this in mind, the balloon is constructed as a pre-curved, low pressure, high volume balloon as disclosed in commonly owned U.S. patent application Ser. No. 11/364,363, entitled "PRECURVED GASTRIC BAND", filed Mar. 1, 2006, which is incorporated herein by reference. The balloon is constructed to maintain a soft and flexible surface (low pressure) when applied to the stomach tissue. The balloon is also constructed to provide 360 degree coverage to prevent tissue pinching or discontinuities in stomach shape, and, as such, may employ the balloon construction disclosed in commonly owned U.S. patent application Ser. No. 11/182,070, filed Jul. 15, 2005, entitled "GASTRIC BAND WITH MATING END PROFILES", which is incorporated herein by reference. The balloon is further constructed such that it reaches its fully inflated and encircling configuration with minimal "folds". In addition, the balloon is constructed to exhibit no folds or creases (single axis, not dual axis) when all fluid is evacuated therefrom.

As those skilled in the art will certainly appreciate, and with reference to FIG. 1, a supply tube 50 is used to connect the internal cavity of the balloon 14 of the gastric band 10 with a fluid injection port 52, for example, a velocity port. The utilization of the supply tube 50 with a remote fluid injection source 52 allows for controlled inflation and deflation of the balloon 14 in a predetermined manner. The exact position of the supply tube 50 is important in that the surgeon does not want tubing to be a visual obstruction during locking and/or other manipulation of the gastric band 10. In addition, once placement of the gastric band 10 is complete, the supply tube 50 should not cause irritation to surrounding tissue (for example, sticking directly into the liver or spleen). Surgeons also do not want to pull the supply tube 50 through a retrogastric tunnel, since they cannot easily see if the tissue is being damaged. The supply tube 50 should also be able to act as a safe grasping location for manipulation of the gastric band 10, the supply tube 50 must not kink at the junction to the gastric band 10 and prevent fluid flow, and the supply tube location should facilitate passage of the gastric band 10 through a small trocar.

In accordance with various preferred embodiments of the present invention, different tube placements may be employed as disclosed in commonly owned U.S. patent application Ser. No. 11/364,362, filed Mar. 1, 2006, entitled "Gastric Band", which is incorporated herein by reference.

Although the present invention is described for use in conjunction with gastric bands, those skilled in the art will appreciate the above invention has equal applicability to other types of implantable bands. For example, bands used for the treatment of fecal incontinence. One such band is described in U.S. Pat. No. 6,461,292. Bands can also be used to treat urinary incontinence. One such band is described in U.S. Patent Application Publication No. 2003/0105385. Bands can also be used to treat heartburn and/or acid reflux. One such band is described in U.S. Pat. No. 6,470,892. Bands can also be used to treat impotence. One such band is described in U.S. Patent Application Publication No. 2003/0114729.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A balloon-type gastric band, comprising:
a balloon and a belt secured to the balloon;
the balloon including at least one radiopaque and colored section allowing for postoperative visualization by an external diagnostic tool and actual visualization during a surgical procedure and at least one clear section, which is transparent and optically translucent, allowing for postoperative visualization by an external diagnostic tool and actual visualization during a surgical procedure, the at least one radiopaque and colored section and the at least one clear section facilitating contrasting the balloon from surrounding tissue when placed within a patient and facilitating identification of leaks within the balloon.

2. The balloon-type gastric band according to claim 1, wherein the at least one radiopaque and colored section is a spiral.

3. The balloon-type gastric band according to claim 1, wherein the at least one radiopaque and colored section is a stripe.

4. The balloon-type gastric band according to claim 1, wherein the at least one radiopaque and colored section includes a colored pad print.

5. The balloon-type gastric band according to claim 1, wherein laterally opposed sides of the balloon are provided with radiopaque and colored sections.

6. The balloon-type gastric band according to claim 1, further including a colored pad print.

7. A balloon-type gastric band, comprising:
a balloon having an inner surface and an outer surface, and a belt having an inner surface and an outer surface, the inner surface of the belt being secured to the outer surface of the balloon;
wherein at least one of the balloon or the belt is clear and optically translucent, allowing for postoperative visualization by an external diagnostic tool and actual visualization during a surgical procedure, and the other is radiopaque and colored allowing for postoperative visualization by an external diagnostic tool and actual visualization during a surgical procedure.

8. The balloon-type gastric band according to claim 7, wherein the belt is clear and the balloon is colored.

9. The balloon-type gastric band according to claim 8, wherein the balloon is clear and the belt is colored.

10. A balloon-type gastric band, comprising:
a balloon and a belt secured to the balloon;
the balloon is colored for actual visualization during a surgical procedure while remaining optically translucent, the balloon being composed of a material into which a radiopaque contrast agent is incorporated thus allowing for postoperative visualization by an external diagnostic tool and actual visualization during a surgical procedure; and
the belt is clear, transparent and optically translucent allowing for postoperative visualization by an external diagnostic tool and actual visualization during a surgical procedure.

* * * * *